US008123817B2

(12) United States Patent  
Intoccia et al.

(10) Patent No.: US 8,123,817 B2  
(45) Date of Patent: Feb. 28, 2012

(54) MESHES OF VARIABLE CONSTRUCTION

(75) Inventors: Alfred Intoccia, Nashua, NH (US); Jianmin Li, Lexington, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 486 days.

(21) Appl. No.: 12/343,737

(22) Filed: Dec. 24, 2008

(65) Prior Publication Data

US 2009/0171377 A1 Jul. 2, 2009

Related U.S. Application Data

(60) Provisional application No. 61/009,455, filed on Dec. 28, 2007.

(51) Int. Cl.
*A61F 2/02* (2006.01)
*A61B 17/08* (2006.01)

(52) U.S. Cl. .................... 623/23.72; 606/151

(58) Field of Classification Search .............. 606/151; 623/23.72, 23.75, 23.76; 600/37; 424/422–424
See application file for complete search history.

(56) References Cited

U.S. PATENT DOCUMENTS

| | | | | |
|---|---|---|---|---|
| 5,686,090 | A | * | 11/1997 | Schilder et al. ............. 424/423 |
| 6,120,539 | A | * | 9/2000 | Eldridge et al. ............. 600/37 |
| 6,652,595 | B1 | * | 11/2003 | Nicolo ..................... 623/23.72 |
| 6,666,817 | B2 | | 12/2003 | Li |
| 2005/0010239 | A1 | | 1/2005 | Chefitz |
| 2005/0038451 | A1 | | 2/2005 | Rao et al. |
| 2005/0096499 | A1 | | 5/2005 | Li et al. |
| 2006/0116696 | A1 | | 6/2006 | Odermatt et al. |
| 2006/0199996 | A1 | | 9/2006 | Caraballo et al. |
| 2006/0205998 | A1 | | 9/2006 | Li et al. |
| 2007/0282160 | A1 | | 12/2007 | Sheu et al. |

FOREIGN PATENT DOCUMENTS

| | | |
|---|---|---|
| WO | 0074633 A2 | 12/2000 |
| WO | 0145588 A2 | 6/2001 |
| WO | 02098322 A1 | 12/2002 |
| WO | 2007097994 A2 | 8/2007 |
| WO | 2008058163 A2 | 5/2008 |

OTHER PUBLICATIONS

Bernd Klosterhalfen et al., "The lightweight and large porous mesh concept for hernia repair," Expert Rev. Med. Devices, 2005, 2(1)103-117.
Pelvic Floor Disorders. The Merck Manuals Online Medical Library, Home Edition. www.merck.com. May 9, 2007 download.
J.W.A. Burger et al, "Evaluation of new prosthetic meshes for ventral hernia repair," Surg. Endosc., 2006, 20: 1320-1325.
Fred E. Govier et al, "Pubovaginal slings: a review of the technical variables," Current Opinion in Urology, 2001, 11:405-410.
Renaud De Tayrac et al., "Collagen-coated vs noncoated low-weight polypropylene meshes in a sheep model for vaginal surgery. A pilot study," International Urogynecology Journal, 2007, 18:513-520.
A.J. Duffy et al., "Comparison of two composite meshes using two fixation devices in a porcine laparoscopic ventral hernia repair model," Hernia, 2004, 8:358-364.
John Klutke et al., "The promise of tension-free vaginal tape for female SUI," Contemporary Urology, Oct. 2000, pp. 59-73.

* cited by examiner

*Primary Examiner* — Julian Woo

(57) ABSTRACT

According to one aspect, the present invention provides a substantially two-dimensional surgical mesh comprising a base material, a first area having a first characteristic and a second area having a second characteristic that differs from the first characteristic. The surgical mesh may further comprise a third area having a third characteristic that may be the same as or different from the first and second characteristics, and so on.

21 Claims, 3 Drawing Sheets

MESHES OF VARIABLE CONSTRUCTION

STATEMENT OF RELATED APPLICATION

This application claims the benefit of U.S. Provisional Patent Application Ser. No. 61/009,455, filed Dec. 28, 2007, entitled "Meshes of Variable Construction," which is incorporated herein by reference in its entirety.

FIELD OF THE INVENTION

The present invention relates to surgical meshes and more particularly to surgical meshes of variable construction.

BACKGROUND INFORMATION

Urinary incontinence affects millions of men and women of all ages in the United States. Stress urinary incontinence (SUI) affects primarily women and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.). The result is that there is an insufficient response time to promote urethral closure and, consequently, urine leakage and/or flow results. A popular treatment of SUI is via the use of a surgical mesh, commonly referred to as a sling, which is permanently placed under a patient's bladder neck or mid-urethra to provide a urethral platform. Placement of the sling limits the endopelvic fascia drop, while providing compression to the urethral sphincter to improve coaptation. Further information regarding sling procedures may be found, for example, in the following: Fred E. Govier et al., "Pubocaginal slings: a review of the technical variables," *Curr. Opin Urol.* 11:405-410, 2001, John Klutke and Carl Klutke, "The promise of tension-free vaginal tape for female SUI," *Contemporary Urol.* pp. 59-73, October 2000; and PCT Patent Publication No. WO 00/74633 A2: "Method and Apparatus for Adjusting Flexible Areal Polymer Implants."

Pelvic floor (pelvic support) disorders involve a dropping down (prolapse) of the bladder, rectum, or uterus caused by weakness of or injury to the ligaments, connective tissue, and muscles of the pelvis. The different types of pelvic floor disorders are named according to the organ affected. For example, a rectocele develops when the rectum drops down and protrudes into the back wall of the vagina. An enterocele develops when the small intestine and the lining of the abdominal cavity (peritoneum) bulge downward between the uterus and the rectum or, if the uterus has been removed, between the bladder and the rectum. A cystocele develops when the bladder drops down and protrudes into the front wall of the vagina. In prolapse of the uterus (procidentia), the uterus drops down into the vagina. See, e.g., The Merck Manuals Online Medical Library, Home Edition, "Pelvic Floor Disorders," www.merck.com. As with SUI, treatment of pelvic floor disorders are commonly treated by permanently implanting a surgical mesh within the patient's pelvis to support the organ or organs that require support.

Further uses of surgically implantable meshes include hernia meshes (e.g., meshes for inguinal hernia, hiatus hernia, etc.), meshes for thoracic wall defects, breast support meshes and various other soft-tissue surgical mesh support devices, including meshes for cosmetic & reconstructive surgery, among others.

Due to deficiencies in prior art meshes, improved surgical meshes are needed.

SUMMARY OF THE INVENTION

According to one aspect, the present invention provides a substantially two-dimensional surgical mesh comprising a base material, a first area having a first characteristic and a second area having a second characteristic that differs from the first characteristic. The first and second areas may vary, for example, in tissue response, mechanical properties and/or appearance. The surgical mesh may further comprise a third area having a third characteristic that may be the same as or different from the first and second characteristics, and so on.

These and other aspects, as well as various embodiments and advantages of the present invention will become readily apparent to those of ordinary skill in the art upon review of the Detailed Description to follow.

DETAILED DESCRIPTION

Figure 1:
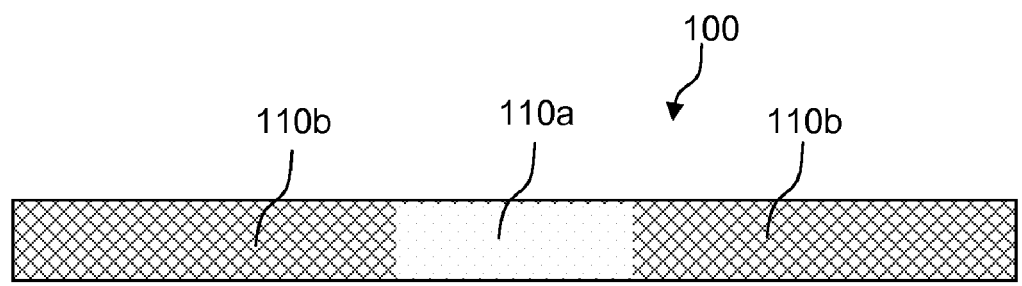
FIGS. 1 and 2 are schematic plan views of a substantially rectangular surgical mesh, in accordance with two embodiments of the invention.

According to one aspect, the present invention provides a substantially two-dimensional surgical mesh comprising a base material (e.g., a biocompatible polymeric material, for instance, composed of one or more biocompatible polymeric fibers), a first area having a first characteristic and a second area having a second characteristic that differs from the first characteristic. For example, the first and second areas may be formed from the same base material, but have different knitting characteristics to vary the mechanical properties of the areas (e.g., variations in tensile strength, flexibility, etc.).

As another example, the first area may consist essentially of the base material or may be provided with a first material, while the second area may consist essentially of the base material or may be provided with a second material. The first and second materials (e.g., biologic sourced materials, biodegradable materials, etc.) may be provided, for example, to improve tissue responses or mesh visibility, among other purposes. The mesh may further comprise a third area that may consist essentially of the base material or may be provided with a third material, and so forth. The first, second, third, etc. materials may be the same or different, and they may be selected, for example, from (a) materials that promote tissue response (and thus tissue integration), (b) materials having bioinert properties (and thus generate little tissue response), (c) materials that block tissue ingrowth, either temporarily or permanently, (d) materials that reduce tissue adhesions, (e) materials that reduce tissue erosion, (f) materials that promote bonding of the mesh to target tissue, (g) biodegradable materials, (h) materials having different color for placement and identification purposes, and (i) combinations of two or more of the foregoing materials.

As used herein a "substantially two-dimensional" object is a sheet-like object, typically one whose length and width are at least 10 times greater than the thickness of the material forming the object, for example, whose length and width are each 10 to 25 to 50 to 100 or more times the thickness. For example, surgical meshes may be in the form of ribbons, sheets, and other more complex sheet-like shapes (see, e.g., FIGS. 3 to 6 below). In many embodiments, the mesh will be able to take on a planar configuration, for example, when placed on a planar surface such as a table top. However, substantially two-dimensional objects, including the surgical meshes of the invention, need not be planar. For example, such objects may curve in space (e.g., as a substantially two-dimensional orange peel curves around the inner portion of the orange, etc.).

Surgical meshes in accordance with the present invention are typically formed using one or more filaments (e.g., fibers, fibrils, threads, yarns, etc.). Thus, surgical meshes in accordance with the present invention include monofilament and multifilament meshes. Surgical meshes in accordance with the present invention include woven meshes and non-woven meshes (including knitted meshes, felt meshes, and spun-bound meshes, among others). Surgical meshes in accordance with the present invention include meshes having small pores (less than 1 mm) and those having large pores (greater than or equal to 1 mm). In many embodiments, the surgical meshes of the invention have pore sizes greater than about 5 microns in diameter.

Filaments for forming meshes in accordance with the present invention are generally polymeric filaments which remain intact in vivo (i.e., non-bioresorbable polymeric filaments), and include those formed from (a) polyolefins, including homopolymers and copolymers of C1-C8 alkenes, for example, polypropylene, (b) fluoropolymers, including homopolymers and copolymers of C1-C8 alkenes in which one or more hydrogen atoms are substituted with fluorine, for example, polytetrafluoroethylene and polyvinylidene fluoride, and (c) polyesters, including, for example, polyethylene terephthalate, among various other polymers.

As noted above, surgical meshes in accordance with the present invention may be provided with at least first and second materials in some embodiments. The materials may be associated with the meshes in various ways, including the following, among others: (a) loaded into the interior (bulk) of the filaments, (b) bound to the surface of the filaments by covalent interactions and/or non-covalent interactions (e.g., interactions such as van der Waals forces, hydrophobic interactions and/or electrostatic interactions, for instance, charge-charge interactions, charge-dipole interactions, and dipole-dipole interactions, including hydrogen bonding), (c) applied as a coating (biostable or biodegradable) that at least partially surrounds the mesh filament(s) but does not fill the pores of the mesh, (d) applied as a coating (biostable or biodegradable) that at least partially surrounds the mesh filament(s) and fills the pores of the mesh, (e) physically woven into or physically attached (e.g., sewn or sutured) to the mesh, and (f) combinations of the forgoing.

As also noted above, the materials may be selected, for example, from (a) materials that promote tissue response, (b) materials having bioinert properties, (c) materials that temporarily or permanently block tissue ingrowth, (d) materials that reduce tissue adhesions, (e) materials that reduce tissue erosion, (f) materials that promote bonding of the mesh to target tissue (e.g., materials that stick to target tissue to stabilize the mesh during implantation), (g) biodegradable materials, (h) materials having different color for placement and identification purposes, and (i) combinations of two or more of the foregoing materials. Some of the previous categories of materials may overlap for a given material.

Materials that promote tissue response (and thus tissue integration) include materials that promote growth of collagenous tissue, such as scar tissue. Examples of such materials include certain biodegradable polymers, for instance, biodegradable polyesters such as polylactide (PLA), polyglycolide (PLG), and poly(lactide-co-glycolide) (PLGA), among many others, which produce inflammation as they degrade due to pro-inflammatory breakdown products, leading to the formation of collagenous tissue such as scar tissue. The rate and degree of biodisintegrable polymer breakdown can depend upon a number of factors including monomer content (e.g., choice of monomer or ratio of monomers, if a copolymer), degree of crystallinity, polymer architecture, exposed surface area, and so forth. Other polymers include alginate, chitin, hyaluronic acid, collagen, and proteins that promote a tissue inflammatory response, thereby promoting healing and tissue integration. Further specific examples of materials that promote collagenous tissue growth may be selected, for instance, from growth factors (e.g., transforming growth factor beta (TGF-beta), epidermal growth factor (EGF), platelet-derived growth factor (PDGF), insulin-like growth factor (IGF), basic fibroblast growth factor (bFGF), vascular endothelial growth factor (VEGF), etc.) and other materials such as cytokines (i.e., substances made by cells that are used by the same, or other cells, to produce some type of response), endotoxins, chemokines, prostaglandins, lipid mediators and other mitogens, various natural and synthetic proinflammatory agents, sclerosing agents, cells, including stem cells and other suitable cells derived from the host patient, including fibroblast, myoblast and/or other progenitor cells, among other materials. See, e.g., Pub. No. US2006/0205998 and the references cited therein.

Materials having bioinert properties (and thus generate little tissue response) may be selected, for example, from styrene-isobutylene copolymers, including block copolymers such as poly(styrene-b-isobutylene-b-polystyrene), polyurethanes, and fluoropolymers such as polytetrafluoroethylene and polyvinylidene fluoride. As noted above, materials that promote a tissue response are desirable in some embodiments (or in some areas of the mesh). However, in other embodiments (or in other areas of the mesh), materials that promote a tissue response are less desirable, even undesirable. For example, mesh shrinkage is known to commonly occur after implantation—not as a result of shrinkage in the mesh material itself, but rather as a result of the contraction of scar tissue around the mesh. See, e.g., B. Klosterhalfen et al., "The lightweight and large porous mesh concept of hernia repair," Expert. Rev. Med. Devices 2005 2(1) 103-117. For hernia meshes, shrinkage is undesirable in that long-term hernia repairs in that the hernia gap may become insufficiently covered over time, leading to recurrence. Id. Moreover, shrinkage can increase the pressure that the mesh exerts on various organs, potentially leading to erosion. Therefore, in certain embodiments, materials having bioinert properties are desired in order to minimize the body's inflammatory responses (which as previously noted, lead to the formation of collagenous tissue such as scar tissue) and delay tissue integration with the mesh. In these embodiments, the mesh may be incorporated into (i.e., surrounded by) tissue, although preferably tissue other than scar tissue, or tissue having substantially reduced amounts of scar tissue.

In certain embodiments, an anti-inflammatory material, for example, a steroidal or non-steroidal anti-inflammatory agent, may be provided along with the bioinert material to further minimize the body's inflammatory response. In other embodiments, a hormonal material such as estrogen, for example, may be provided to promote the formation of organized collagen tissue instead of random scar tissue.

Materials that block tissue ingrowth include materials that are capable of filling the pores of the mesh. For example, tissue ingrowth may be temporarily blocked using a bioerodable polymer selected, for example, from natural bioerodable polymers such as carboxymethylcellulose (CMC) and alginate (which may be ionically crosslinked with bivalent cations such as calcium ions), among others, and from synthetic bioerodable polymers such as PLA, PGA or PLGA, among others. Tissue ingrowth may be permanently blocked using a biostable natural or synthetic polymer selected, for example, from natural biostable polymers such as natural rubber, among others, and from synthetic biostable polymers such as polyurethanes, polyesters, polypropylene, among others.

Materials that reduce tissue adhesions include materials such as a collagen (see A. J. Duffy, *Hernia*, December 2004, 8(4):358-64), collagen-polyethylene glycol-glycerol (see, J. W. Burger et al., *Surg. Endosc.*, August 2006 (Epub Jul. 24, 2006), 20(8): 1320-5), carboxymethylcellulose, sodium hyaluronate, and carboxymethylcellulose-sodium hyaluronate, among others.

Materials that reduce tissue erosion include materials such as collagen (see R. de Tayrac et al., *Int. Urogynecol. J. Pelvic Floor Dysfunct.*, May 2007 (Epub Aug. 29, 2006), 18(5):513-20) CMC and hyaluronic acid, among others.

Materials that promote bonding of the mesh to target tissue (e.g., to assist in maintaining the positioning of the mesh in the body prior to and/or during suturing) include, for example, materials that promote bonding of the mesh to target tissue upon contact (e.g., based on wetting due to blood or application of saline, calcium chloride solutions, other solutions, etc.) such as hydrophilic materials (e.g., collagen, carboxymethyl cellulose, various mucoadhesives, flouronic type polymers, etc.), coagulation components (e.g., thrombin, fibrinogen, etc.), ionically crosslinkable materials (e.g., alginate, etc.), and so forth. Further examples of materials that promote bonding of the mesh to target tissue include fibrin glue. In preferred embodiments the bond that is established between the mesh and the tissue is sufficiently reversible to allow the mesh to be repositioned after initial placement, yet sufficiently strong to maintain the mesh in position during suturing.

Examples of biodegradable materials include PLA, PGA and PLGA.

Examples of materials having different color for placement and identification purposes include various biocompatible inks and dyes.

In addition to the above-described materials, meshes in accordance with the present invention may be provided with further supplemental agents such as analgesic agents, anesthetic agents, antibiotic agents, and antimicrobial agents, among others.

Specific embodiments of the invention will now be discussed in conjunction with the drawings. For example, FIG. 1 schematically illustrates an elongated mesh 100 (e.g., a midurethral sling or a striplet to support soft tissue). A first area of the mesh, in particular, the central portion 110a of the mesh 100 may be untreated (e.g., consisting of non-bioresorbable polymeric filament materials such as polypropylene, polytetrafluoroethylene, polyvinylidene fluoride, polyethylene terephthalate, etc.), may be provided with a material that promotes tissue response, may be provided with a material that reduces tissue erosion, may be provided with a material having bioinert properties, may be provided with a material that temporarily blocks or delays tissue ingrowth, may be provided with a biodegradable material, or may be provided with a material that has different color for placement and identification, among other possibilities. Independently of the central portion 100a, second areas of the mesh, in particular, the two arms 110b of the mesh 100, may be untreated, provided with a material that promotes tissue ingrowth (e.g., a material that promotes tissue response, and thus tissue integration), provided with a material that has different color for placement and identification or provided with a material that promotes bonding of the mesh to target tissue, among other possibilities.

Figure 2:
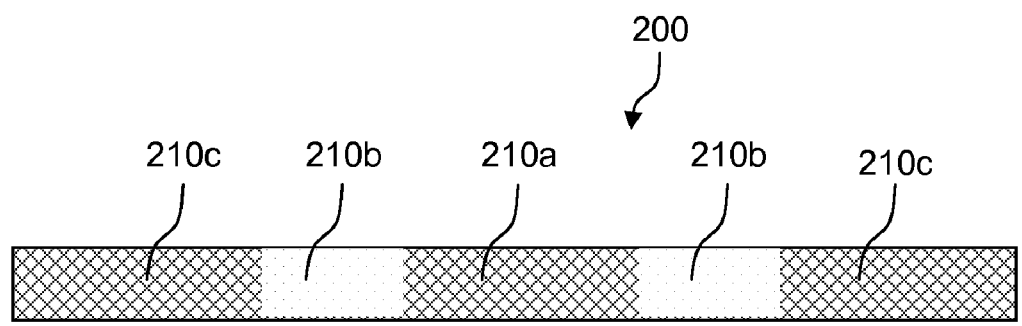

As another example, there is schematically illustrated in FIG. 2 an elongated mesh 200. A first area of the mesh, in particular, the central portion 210a of the mesh 200, may be untreated, provided with a material that reduces tissue erosion, provided with a material having bioinert properties, provided with a material that temporarily blocks or delays tissue ingrowth, provided with a material that reduces tissue erosion, or provided with a material that promotes bonding of the mesh to target tissue, among other possibilities. Independently of the central portion 210a, second areas of the mesh, in particular, areas 210b, may be untreated, provided with a material that promotes tissue response, provided with a material having bioinert properties, provided with a material that temporarily blocks tissue ingrowth, or provided with a material that reduces tissue erosion, among other possibilities. Independently of the central portion 210a and the areas 210b, third areas of the mesh, in particular, areas 210c, may be provided with a material that has a different color as placement indicator, may be provided with a material that promotes tissue response, or may be provided with a material that promotes bonding of the mesh to target tissue, among other possibilities.

Figure 3:
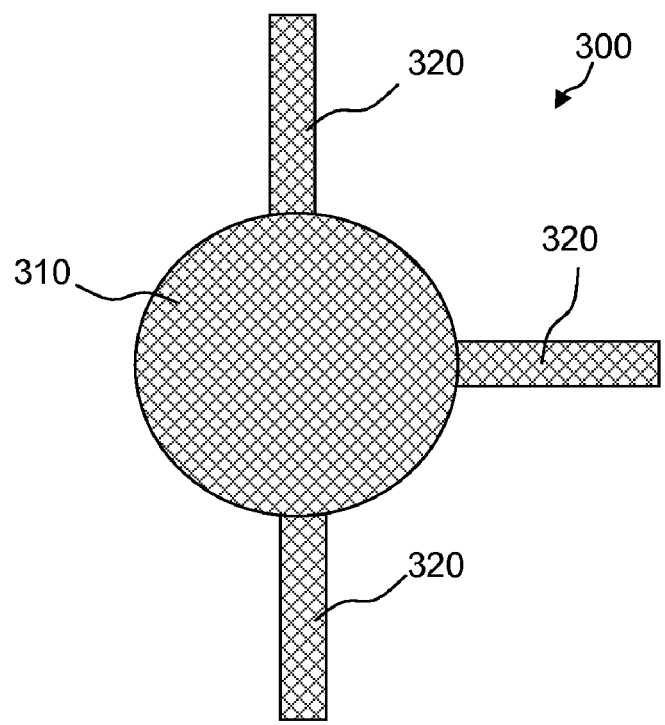
FIGS. 3-6 are schematic plan views of surgical meshes which have a central body portion from which a plurality of arms emanate, in accordance with various additional embodiments of the invention.

As another example, there is schematically illustrated in FIG. 3, a mesh 300 having a body portion 310 and a plurality of arms 320 that emanate from the body portion 310, for example, a pelvic floor mesh. The body portion 310 of the mesh structure 300 may be untreated, provided with a material that reduces tissue erosion, provided with a material having bioinert properties, provided with a material that temporarily blocks or delays tissue ingrowth, provided with material that is biodegradable, or provided with a material that has different color for placement and identification, among other possibilities. Independently of the central portion 310, the arms 320 of the mesh structure 300 may be untreated, treated with a material that promotes tissue response, or provided with a material that promotes bonding of the mesh to target tissue, among other possibilities.

Figure 4:
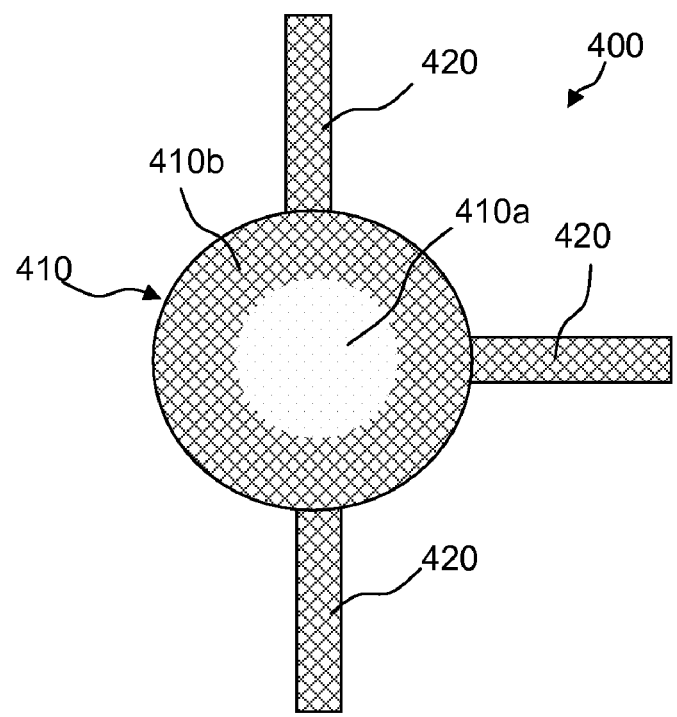

As another example, there is schematically illustrated in FIG. 4 a mesh 400 having a first area (i.e., a inner portion 410a of the central body 410 of the mesh structure), a second area (i.e., an outer portion 410a of the central body 410 of the mesh structure), and a plurality of third areas (i.e., arms 420 that emanate from the central portion 410). The inner portion 410a of the central body 410 of the mesh structure 400 may be, for example, untreated, provided with a material that reduces tissue erosion, provided with a material that reduces adhesions, provided with a material having bioinert properties, provided with a material that temporarily blocks or delays tissue ingrowth, provided with a material that is biodegradable, or provided with a material that has different color for placement and identification, among other possibilities. Independently of the inner portion 410a, the outer portion 410b of the central body 410 of the mesh structure 400 may be untreated, provided with a material that reduces tissue erosion, provided with a material that reduces adhesions, provided with a material having bio-inert properties, or provided with a material that temporarily blocks tissue ingrowth, among other possibilities. Independently of the inner and outer portions 410a, 410b of the central body 410, the arms 420 of the mesh structure 400 may be untreated, provided with a material that promotes tissue response, provided with a material having bioinert properties, or provided with a material that promotes bonding of the mesh to target tissue, among other possibilities.

It is noted that although the meshes in FIGS. 3 and 4 above have a circular central portion, essentially any size and shape central portion can be used (e.g., so long as it is of sufficient dimension to conduct pelvic floor repair within the body). Moreover, although the meshes of FIGS. 3 and 4 have rectangular arms, they may be of essentially any size and shape (e.g., as long as they are of sufficient length and width to hold the central portion within the body). Furthermore, although the meshes of FIGS. 3 and 4 have three arms, other numbers of arms may be used (e.g., 1, 2, 4, 5, 6, 7, 8, etc.). As one specific variation FIG. 5 illustrates a mesh 500 having a non-circular (oval) central body portion 510 with inner portion 510a and outer portion 510b and six non-rectangular (trapezoidal) arms 520, among near limitless other possibilities.

Figure 5:
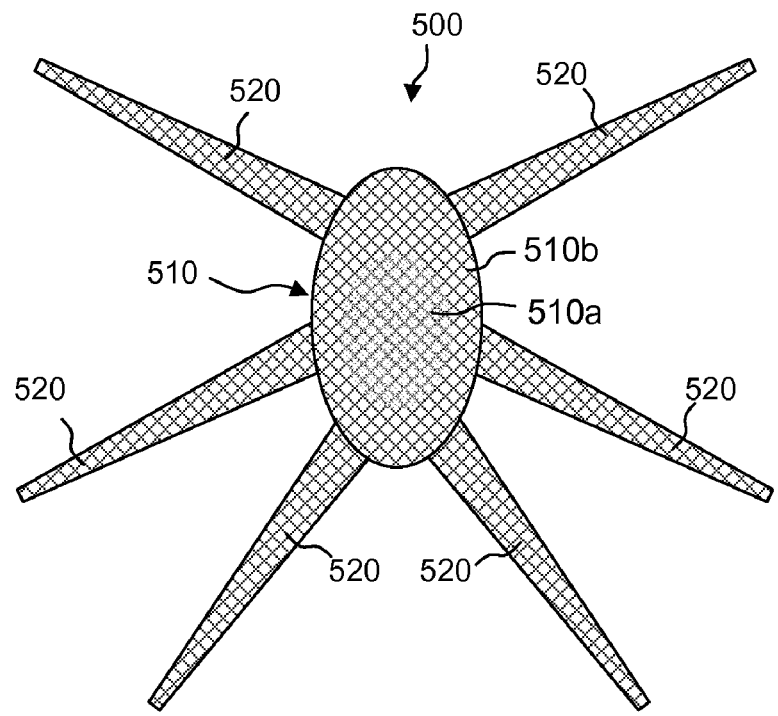
Figure 6:
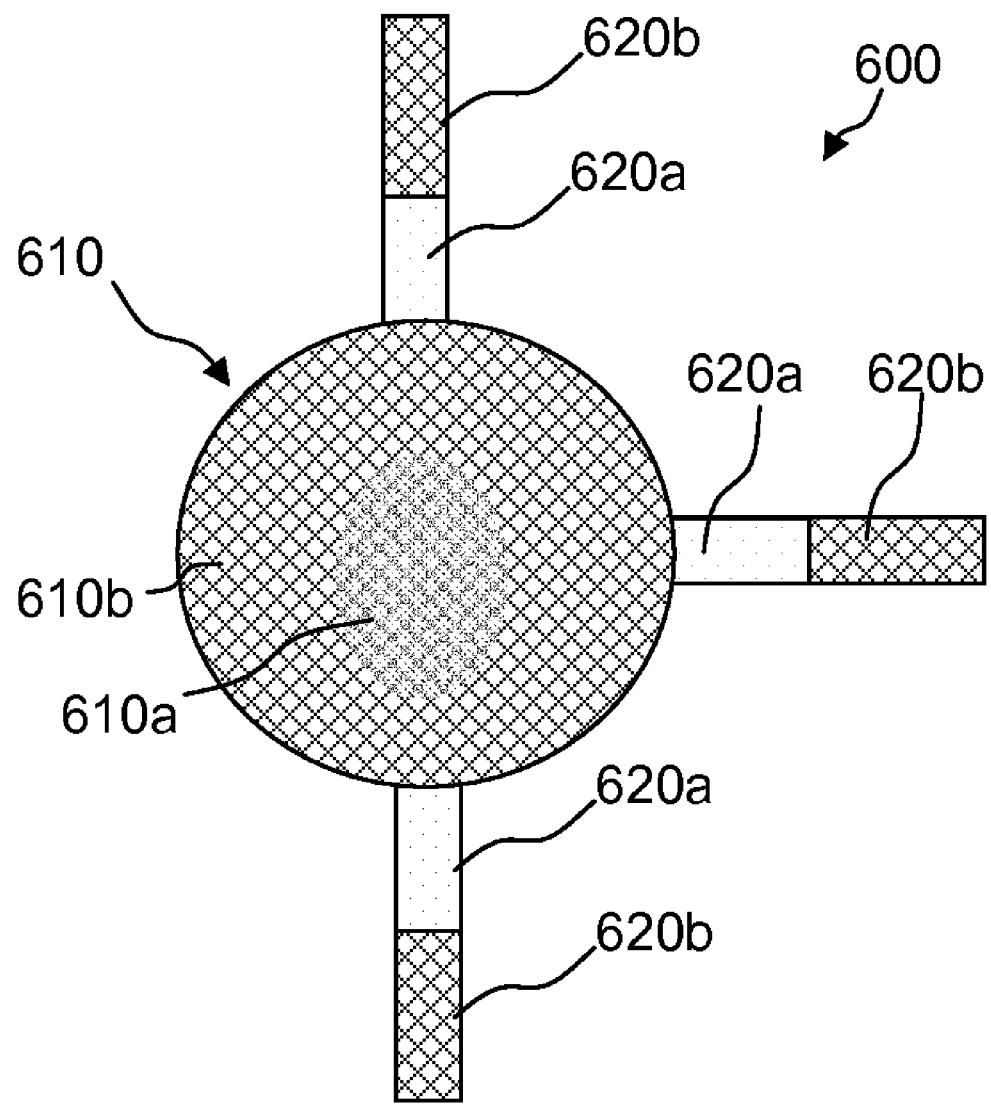

In addition, although the meshes of FIGS. 3-5 have arms that are of constant composition along their length, this need not be the case. As one specific variation FIG. 6 illustrates a mesh 600 having a non-circular (oval) central body portion 610 with inner portion 610a and outer portion 610b and three arms, each having an inner portion 620a and an outer end portion 620b, which may be independently untreated or provided with one of the materials described above, among other possibilities.

Various aspects of the invention relating to the above are enumerated in the following paragraphs:

Aspect 1. A substantially two-dimensional surgical mesh comprising a base material, a first area that is provided with a first material and a second area that is provided with a second material, wherein the first and second materials are different from one another, and wherein the first and second materials are selected from (a) materials that promote a tissue response, (b) materials having bioinert properties, (c) materials that block or delay tissue ingrowth, (d) materials that reduce tissue adhesions, (e) materials that reduce tissue erosion, (f) materials that promote bonding of the mesh to adjacent tissue, (g) biodegradable materials, and (h) materials that generate distinctive color from other portion of the mesh.

Aspect 2. The surgical mesh of aspect 1, further comprising a third area which is provided with a third material which may be the same or different from the first material and the same or different from the second material.

Aspect 3. The surgical mesh of aspect 1, wherein the mesh comprises a knitted construction.

Aspect 4. The surgical mesh of aspect 1, wherein the mesh comprises a woven construction.

Aspect 5. The surgical mesh of aspect 1, wherein the mesh comprises pores greater than or equal to 5 microns in width.

Aspect 6. The surgical mesh of aspect 1, wherein the base material comprises a non-bioresorbable polymeric filament that comprises a polymer selected from a polyolefin, a fluoropolymer, a polyester, and combinations thereof.

Aspect 7. The surgical mesh of aspect 1, wherein the base material comprises a non-bioresorbable polymeric filament that comprises a polymer selected from a polypropylene, polytetrafluoroethylene, polyvinylidene fluoride, polyethylene terephthalate, and combinations thereof.

Aspect 8. The surgical mesh of aspect 1, wherein the base material comprises a mesh filament and wherein the first and second materials are independently (a) disposed within the interior of the mesh filament, (b) attached to the surface of the mesh filament, (c) applied as coating that at least partially surrounds the mesh filament and does not fill the pores of the mesh, (d) applied as a biostable or bioresorbable coating that at least partially surrounds the mesh filament and at least partially fills the pores of the mesh, or (e) physically woven into or physically attached to the mesh filament.

Aspect 9. The surgical mesh of aspect 1, wherein the first and second materials are selected from (a) a material that promotes a tissue response selected from biodegradable polymers, growth factors, and combinations thereof, (b) a material having bioinert properties selected from fluoropolymers, polyurethanes, and combinations thereof, (c) a material that temporarily blocks tissue ingrowth selected from carboxymethyl cellulose, hyaluronic acid, alginate, and combinations thereof, (d) a material that reduces tissue adhesions selected from carboxymethyl cellulose, hyaluronic acid, collagen, and combinations thereof, (e) a material that reduce tissue erosion selected from carboxymethyl cellulose, hyaluronic acid, collagen, and combinations thereof, and (f) materials that promote bonding of the mesh to adjacent tissue selected from fibrinogen.

Aspect 10. The surgical mesh of aspect 1, wherein the mesh comprises an elongated mesh body.

Aspect 11. The surgical mesh of aspect 1, wherein the mesh comprises a central mesh portion comprising an area comprising said first material and a plurality of mesh arms emanating from the central mesh portion, and wherein at least one mesh arm comprise an area comprising said second material.

Aspect 12. The surgical mesh of aspect 11, wherein the first material comprises a material having bioinert properties and said second material comprises a material that promotes a tissue response, a material that promotes bonding of the mesh to tissue, or a combination thereof.

Aspect 13. The surgical mesh of aspect 11, wherein the first material comprises a material that reduces tissue erosion and said second material comprises a material that promotes a tissue response, a material that promotes bonding of the mesh to tissue, or a combination thereof.

Aspect 14. The surgical mesh of aspect 11, wherein the first material comprises a biodegradable material and said second material comprises a material that promotes a tissue response, a material that promotes bonding of the mesh to tissue, or a combination thereof.

Aspect 15. The surgical mesh of aspect 11, wherein the first material comprises a material selected from carboxymethyl cellulose, hyaluronic acid, alginate, collagen, biodegradable polymers, growth factors and combinations thereof and said second material comprises a material selected from biodegradable polymers, growth factors, fibrinogen and combinations thereof.

Aspect 16. The surgical mesh of aspect 11, wherein the central mesh portion further comprises an area that does not comprise said first material.

Aspect 17. The surgical mesh of aspect 11, wherein said at least one mesh arm further comprises an area that does not comprise said second material.

Although various embodiments are specifically illustrated and described herein, it will be appreciated that modifications and variations of the present invention are covered by the above teachings and are within the purview of any appended claims without departing from the spirit and intended scope of the invention.

The invention claimed is:

1. A substantially two-dimensional surgical mesh comprising a base material, said mesh comprising a central body comprising a first area of one side of the mesh that is provided with a first material and a plurality of arms emanating from the central body portion, wherein each of the arms has a width that is less than a width of the central body portion, wherein each of the arms comprises a second area that of said side is provided with a second material independently of said central body portion, wherein the first and second materials are different from one another, and wherein the first and second materials are selected from (a) materials that promote a tissue response, (b) materials having bioinert properties, (c) materials that block or delay tissue ingrowth, (d) materials that reduce tissue adhesions, (e) materials that reduce tissue erosion, (f) materials that promote bonding of the mesh to adjacent tissue, (g) biodegradable materials, and (h) materials that generate distinctive color from other portion of the mesh.

2. The surgical mesh of claim 1, further comprising a third area of said side which is provided with a third material which may be the same or different from the first material or the same or different from the second material.

3. The surgical mesh of claim 1, wherein said mesh comprises a knitted construction.

4. The surgical mesh of claim 1, wherein said mesh comprises a woven construction.

5. The surgical mesh of claim 1, wherein said mesh comprises pores greater than or equal to 5 microns in width.

6. The surgical mesh of claim 1, wherein said base material comprises a non-bioresorbable polymeric filament that comprises a polymer selected from a polyolefin, a fluoropolymer, a polyester, and combinations thereof.

7. The surgical mesh of claim 1, wherein said base material comprises a non-bioresorbable polymeric filament that comprises a polymer selected from a polypropylene, polytetrafluoroethylene, polyvinylidene fluoride, polyethylene terephthalate, and combinations thereof.

8. The surgical mesh of claim 1, wherein said base material comprises a mesh filament and wherein said first and second materials are independently (a) disposed within the interior of the mesh filament, or b) applied as coating that surrounds the mesh filament and does not fill the pores of the mesh.

9. The surgical mesh of claim 1, wherein said first and second materials are selected from (a) a material that promotes a tissue response selected from biodegradable polymers, growth factors, and combinations thereof, (b) a material having bioinert properties selected from fluoropolymers, polyurethanes, and combinations thereof, (c) a material that temporarily blocks tissue ingrowth selected from carboxymethyl cellulose, hyaluronic acid, alginate, and combinations thereof, (d) a material that reduces tissue adhesions selected from carboxymethyl cellulose, hyaluronic acid, collagen, and combinations thereof, (e) a material that reduce tissue erosion selected from carboxymethyl cellulose, hyaluronic acid, collagen, and combinations thereof, and (f) materials that promote bonding of the mesh to adjacent tissue selected from fibrinogen.

10. The surgical mesh of claim 1, wherein the first material comprises a material having bioinert properties and said second material comprises a material that promotes a tissue response, a material that promotes bonding of the mesh to tissue, or a combination thereof.

11. The surgical mesh of claim 1, wherein the first material comprises a material that reduces tissue erosion and said second material comprises a material that promotes a tissue response, a material that promotes bonding of the mesh to tissue, or a combination thereof.

12. The surgical mesh of claim 1, wherein the first material comprises a biodegradable material and said second material comprises a material that promotes a tissue response, a material that promotes bonding of the mesh to tissue, or a combination thereof.

13. The surgical mesh of claim 1, wherein the first material comprises a material selected from carboxymethyl cellulose, hyaluronic acid, alginate, collagen, biodegradable polymers, growth factors and combinations thereof and said second material comprises a material selected from biodegradable polymers, growth factors, fibrinogen and combinations thereof.

14. The surgical mesh of claim 1, wherein said first area of said central body portion is bordered by an area that does not comprise said first material.

15. The surgical mesh of claim 1, wherein each of said arms comprises an area of said side between the second area and the central body portion that does not comprise said second material.

16. The surgical mesh of claim 1, wherein said surgical mesh comprises three or more arms.

17. A substantially two-dimensional surgical mesh comprising a base material that comprises one or more mesh filaments, said mesh comprising a central body comprising a first area of one side of the mesh that is provided with a first material that reduces tissue erosion and a plurality of arms having a width that is less than a width of the central body portion and emanating from the central body portion, wherein each of said arms comprises a second area of said side that is, independently of said central body portion, provided with a second material that promotes tissue ingrowth, that promotes bonding of the mesh to tissue, or a combination thereof, wherein the first and second materials are different from one another.

18. The surgical mesh of claim 17, wherein said first area of the central body portion is bordered by an area that does not comprise said first material.

19. The surgical mesh of claim 17, wherein each of said arms comprises an area between the second area and the central body portion that does not comprise said second material.

20. The surgical mesh of claim 17, wherein said first material is a growth factor.

21. A substantially two-dimensional surgical mesh comprising a base material, said mesh comprising a central body comprising a first area of one side of the mesh that is provided with a first material and three or more arms emanating from the central body portion, wherein each of said arms has a width that is less than a width of the central body portion, wherein each of said arms comprises a second area of said side that is provided with a second material, independently of said central portion, wherein the first and second materials are different from one another, and wherein (i) said first area of the central body portion is bordered by an area that does not comprise said first material and/or (ii) wherein each of said arms comprises an area of said side between the second area and the central body portion that does not comprise said second material.

* * * * *

UNITED STATES PATENT AND TRADEMARK OFFICE
CERTIFICATE OF CORRECTION

| | | |
|---|---|---|
| PATENT NO. | : 8,123,817 B2 | Page 1 of 1 |
| APPLICATION NO. | : 12/343737 | |
| DATED | : February 28, 2012 | |
| INVENTOR(S) | : Intoccia et al. | |

It is certified that error appears in the above-identified patent and that said Letters Patent is hereby corrected as shown below:

In column 9, line 8, in claim 1, delete "area that" and insert -- area --, therefor.

In column 9, line 8, in claim 1, delete "is" and insert -- that is --, therefor.

In column 9, line 43, in claim 8, delete "b)" and insert -- (b) --, therefor.

Signed and Sealed this
Fifteenth Day of May, 2012

David J. Kappos
*Director of the United States Patent and Trademark Office*